(12) United States Patent
Kuwahara et al.

(10) Patent No.: US 10,338,583 B2
(45) Date of Patent: Jul. 2, 2019

(54) DRIVING ASSISTANCE DEVICE

(71) Applicant: MAZDA MOTOR CORPORATION, Hiroshima (JP)

(72) Inventors: Junichiro Kuwahara, Hiroshima (JP); Yohei Iwashita, Hiroshima (JP); Yoko Hoshino, Hiroshima (JP); Ryohei Hisamitsu, Hiroshima (JP); Hitomi Nakazato, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 0 days.

(21) Appl. No.: 15/756,890

(22) PCT Filed: Feb. 24, 2017

(86) PCT No.: PCT/JP2017/007060
§ 371 (c)(1),
(2) Date: Mar. 1, 2018

(87) PCT Pub. No.: WO2017/169386
PCT Pub. Date: Oct. 5, 2017

(65) Prior Publication Data
US 2018/0275652 A1 Sep. 27, 2018

(30) Foreign Application Priority Data
Mar. 31, 2016 (JP) ................ 2016-070612

(51) Int. Cl.
*B62D 6/00* (2006.01)
*G05D 1/00* (2006.01)
(Continued)

(52) U.S. Cl.
CPC ......... *G05D 1/0061* (2013.01); *A61B 5/0077* (2013.01); *A61B 5/18* (2013.01);
(Continued)

(58) Field of Classification Search
CPC ........ B62D 6/007; B62D 15/025; G08G 1/16; B60W 40/08; B60W 50/14
(Continued)

(56) References Cited

U.S. PATENT DOCUMENTS 9,751,534 B2 * 9/2017 Fung ............... B60W 40/08
2016/0041553 A1 2/2016 Sato et al.
(Continued)

FOREIGN PATENT DOCUMENTS

JP H06-255519 A 9/1994
JP H07-069233 A 3/1995
(Continued)

OTHER PUBLICATIONS

International Search Report issued in PCT/JP2017/007060; dated May 23, 2017.

*Primary Examiner* — Tan Q Nguyen
(74) *Attorney, Agent, or Firm* — Studebaker & Brackett PC

(57) ABSTRACT

Disclosed herein is a technique for providing driving assistance for a driver in such a way as to increase the driver's degree of internal focus on driving if his or her degree of internal focus on driving is estimated to be low when deactivation of autonomous driving is predicted. Examples of such driving assistance include boosting the moving vehicle noise to be heard inside the vehicle's cabin, increasing sensitivity to a change in the vehicle's state responsive to driving operations, providing navigation to a road with features that would entertain the driver through driving, and giving guidance in exemplary driving operations.

10 Claims, 9 Drawing Sheets

(51) Int. Cl.
*A61B 5/18*   (2006.01)
*B60W 50/14*  (2012.01)
*B60W 40/08*  (2012.01)
*B62D 15/02*  (2006.01)
*A61B 5/00*   (2006.01)
*G08G 1/16*   (2006.01)
*A61B 5/16*   (2006.01)
*G06K 9/00*   (2006.01)

(52) U.S. Cl.
CPC ............ *B60W 40/08* (2013.01); *B60W 50/14* (2013.01); *B62D 6/007* (2013.01); *B62D 15/025* (2013.01); *A61B 5/168* (2013.01); *A61B 5/7405* (2013.01); *A61B 5/7445* (2013.01); *A61B 2562/0204* (2013.01); *B60W 2540/00* (2013.01); *B60W 2710/30* (2013.01); *G06K 9/00268* (2013.01); *G06K 9/00302* (2013.01); *G08G 1/16* (2013.01)

(58) Field of Classification Search
USPC .......................................................... 701/23
See application file for complete search history.

(56) References Cited

U.S. PATENT DOCUMENTS

| | | | |
|---|---|---|---|
| 2016/0187879 A1* | 6/2016 | Mere .................... | G05D 1/0061 701/23 |
| 2016/0355190 A1 | 12/2016 | Dmi | |
| 2017/0021837 A1 | 1/2017 | Ebina | |
| 2017/0075349 A1 | 3/2017 | Sato et al. | |
| 2017/0220039 A1 | 8/2017 | Funakawa | |
| 2017/0364070 A1* | 12/2017 | Oba ...................... | B60W 50/08 |
| 2018/0022358 A1* | 1/2018 | Fung .................... | B60W 40/08 701/36 |
| 2018/0251128 A1* | 9/2018 | Penilla ................. | B60W 30/09 |

FOREIGN PATENT DOCUMENTS

| | | |
|---|---|---|
| JP | 2014-106854 A | 6/2014 |
| JP | 2015-153048 A | 8/2015 |
| JP | 2016-038768 A | 3/2016 |
| WO | 2015/145606 A1 | 10/2015 |
| WO | 2015/151243 A1 | 10/2015 |

\* cited by examiner

FIG.3

| | | | DRIVER'S CONDITION | | |
|---|---|---|---|---|---|
| | | TENSED (HIGHLY FOCUSED EXTERNALLY) | IDEAL (HIGHLY FOCUSED INTERNALLY) | SELF-DRIVING, AIMLESS (WITH MUCH LEEWAY) | DISTRACTED [INATTENTIVE] (HIGHLY DIVERTED FROM DRIVING) |
| FACE ORIENTATION OFFSET | | SMALL | SMALL | SMALL | LARGE |
| OPERATION OF NAVIGATION SYSTEM, CELLPHONE AND OTHER DEVICES | FREQUENCY | LOW | LOW | LOW | HIGH |
| | DURATION | SHORT | SHORT | SHORT | LONG |
| EYE MOVEMENT VELOCITY | | HIGH | HIGH | LOW | — |
| A/B PEDAL SWITCHING DELAY | | SHORT | SHORT | LONG | — |
| HEAD TURN | | LITTLE | LITTLE | MUCH | — |
| BLINKING | | LITTLE | LITTLE | MUCH | — |
| PUPIL STATE | | WIDE | WIDE | NARROW | — |
| AGREEMENT BETWEEN EYE DIRECTION AND HEAD ORIENTATION | | LOW | HIGH | LOW | — |
| SAME ACCELERATOR POSITION HELD | | SHORT | LONG | SHORT | — |
| A/B PEDAL SWITCHING TIME (DEVIATION) | | LARGE | SMALL | LARGE | — |

DRIVING ASSISTANCE DEVICE

TECHNICAL FIELD

The present invention relates to a driving assistance device.

BACKGROUND ART

Recently, an increasing number of vehicles are equipped with various driving assistance capabilities, examples of which include automatic lane keeping control, automatic braking control, and adaptive auto-cruise control that have already been installed in a lot of vehicles on the market. For example, Patent Document 1 discloses a driving assistance technique for relaxing the driver's attention to the surrounding environment in order to relieve his or her tension. Patent Document 2 discloses a driving assistance technique for alleviating the driver's muscle tone during driving with the intervention of a control program.

CITATION LIST

Patent Documents

PATENT DOCUMENT 1: Japanese Unexamined Patent Publication No. H06-255519
PATENT DOCUMENT 1: Japanese Unexamined Patent Publication No. H07-069233

SUMMARY

Technical Problem

As for the driver's condition during driving, the ideal condition will be a condition in which the driver is driving a vehicle actively enough to keep his or her internal focus on driving high, i.e., a condition in which his or her degree of focus on driving is high and his or her degree of leeway in driving is high.

Meanwhile, autonomous driving vehicles have recently been developed one after another, and will be put on the market soon. There are some different modes of autonomous driving, which include a partially autonomous driving mode with automatic steering and automatic braking capabilities and a fully autonomous driving mode in which everything about vehicle driving, including route selection, is to be determined by the vehicle itself without human intervention. In any case, while such autonomous driving is activated, the driver's load on driving is lightened so much that his or her internal focus on driving tends to decline.

Nevertheless, some unwanted situation is expected where the autonomous driving is abruptly deactivated in the middle due to a significant decline in the detection accuracy of sensors that are essential for the autonomous driving, for example. In such a situation, if the autonomous driving is deactivated while the driver's internal focus on driving has decreased to a rather low level due to his or her overdependence on the autonomous driving, then his or her load on driving steeply increases all of a sudden, thus possibly causing a significant delay in his or her appropriate response in driving operations, and other inconveniences.

In view of the foregoing background, it is therefore an object of the present invention to provide a driving assistance device allowing the driver to substantially avoid, or at least reduce the frequency of occurrence of, such an unwanted situation where the driver's load on driving steeply increases all of a sudden when the autonomous driving is deactivated.

Solution to the Problem

To achieve this object, the present invention proposes the following solutions. Specifically, the present invention provides a driving assistance device for use in a vehicle with autonomous driving capabilities. The device includes:

a degree of internal focus estimating unit configured to estimate a driver's degree of internal focus on driving;

a deactivation predicting unit configured to predict deactivation of autonomous driving; and a driving assistance unit configured to provide driving assistance for the driver in such a way as to increase the driver's degree of internal focus on driving if the degree of internal focus on driving is estimated to be low by the degree of internal focus estimating unit when the deactivation of the autonomous driving is predicted by the deactivation predicting unit.

According to this solution, if the driver's degree of internal focus on driving is low when deactivation of autonomous driving is predicted, then driving assistance is provided for the driver in such a way as to increase the driver's degree of internal focus on driving. This makes the driver fully ready to drive the vehicle by him- or herself when the autonomous driving is deactivated after that, thus substantially avoiding, or at least significantly reducing the frequency of occurrence of, a delay in his or her response in driving operations and other inconveniences.

The following are some exemplary embodiments of the above solution. Specifically, The driving assistance unit may perform a control of increasing sensitivity to a change in the vehicle's state in response to driving operations. According to this embodiment, the same extent of driving operations will cause a more significant change in the vehicle's state, thus motivating the driver to increase his or her degree of internal focus on driving.

The driving assistance unit may provide navigation to a road with features that would entertain the driver through driving. According to this embodiment, having the driver drive along a road to which he or she is guided with navigation will entertain him or her through driving so much to increase his or her degree of internal focus on driving beneficially.

The driving assistance unit may give guidance in exemplary driving operations. According to this embodiment, instructing the driver to drive his or her vehicle following the guidance in exemplary driving as much as possible will not only increase his or her degree of internal focus on driving but also improve his or her driving skills advantageously.

The driving assistance unit may perform control of boosting moving vehicle noise inside the vehicle's cabin. According to this embodiment, such control makes the driver feel the moving vehicle noise even more keenly, thus increasing his or her degree of internal focus on driving.

If the degree of internal focus on driving is estimated to be high by the degree of internal focus estimating unit when the deactivation of the autonomous driving is predicted by the deactivation predicting unit, then the driver may be just notified that the autonomous driving will be deactivated without being provided with any driving assistance by the driving assistance unit, and then the autonomous driving may be deactivated. According to this embodiment, notifying the driver in advance that the autonomous driving will be deactivated soon while quickly performing the autonomous driving deactivation process allows the driver to be conscious, via such an alert beforehand, about the fact that he or she will have to soon start driving the vehicle by him- or herself.

The deactivation predicting unit may predict the deactivation of the autonomous driving according to a degree of accuracy of information available and necessary for the autonomous driving. According to this embodiment, the driver is allowed to be given prediction about the deactivation of autonomous driving both timely and accurately.

Advantages of the Invention

The present invention can substantially avoid, or at least significantly reduce the frequency of occurrence of, an unwanted situation where the driver's load on driving steeply increases all of a sudden when the autonomous driving is deactivated.

BRIEF DESCRIPTION OF THE DRAWINGS

FIG. 3 A table summarizing how the driver's condition is determined to be one of the four different types based on various parameters.

DESCRIPTION OF EMBODIMENTS

Figure 1:
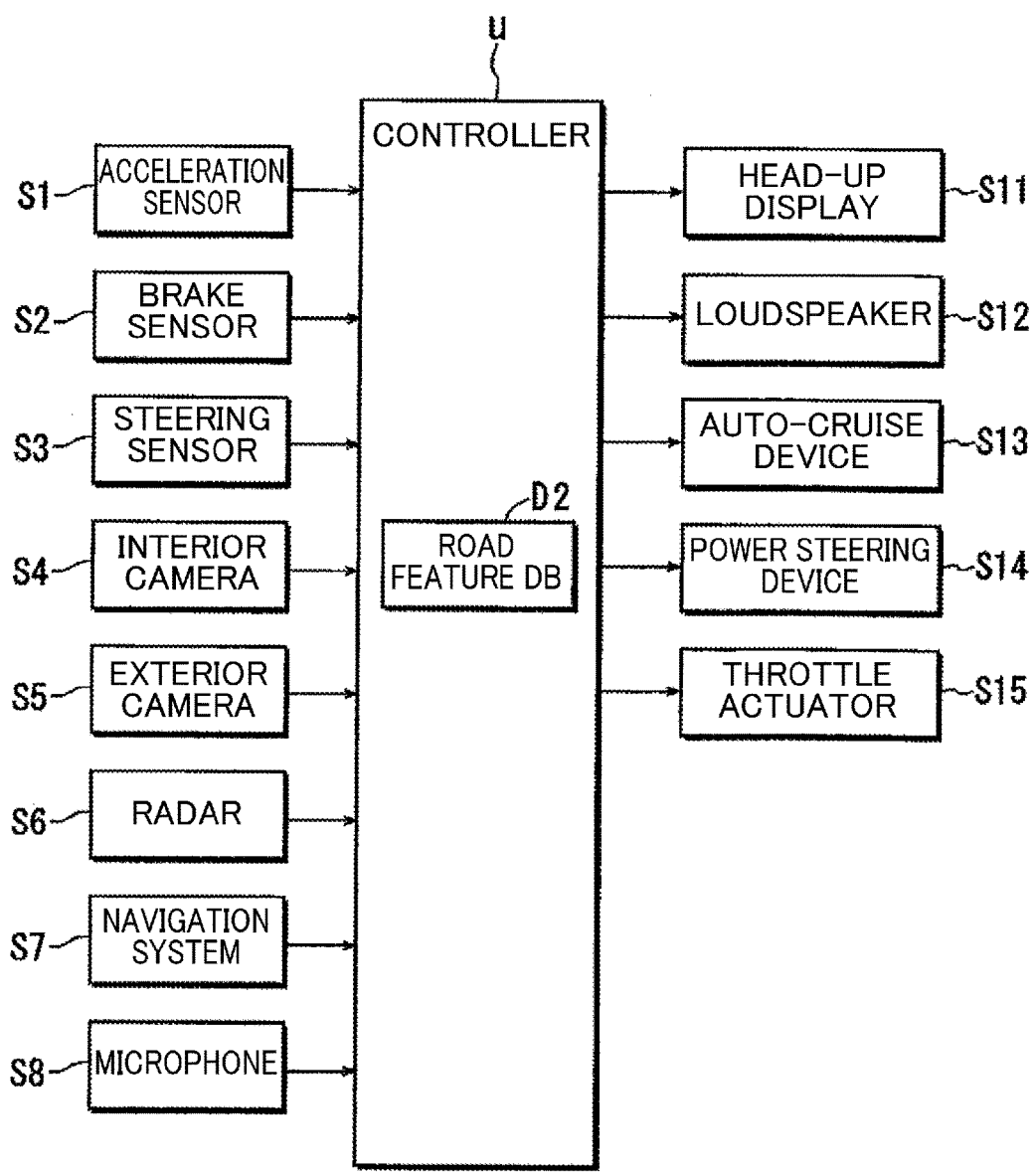
FIG. 1 A block diagram illustrating an exemplary control system according to the present invention.

FIG. 1 illustrates an exemplary control system according to the present invention. As shown in FIG. 1, a controller (control unit) U implemented as a microcomputer receives signals from various sensors and devices S1-S8. Specifically, an acceleration sensor S1 is provided to detect the vehicle's accelerator position. A brake sensor S2 is provided to detect how far the vehicle's brake pedal is depressed (hereinafter referred to as a "degree of depression of the brake pedal"). A steering sensor S3 is provided to detect the steering angle. An interior camera S4 functioning as an image capturing means is provided to capture an image of the driver's face. An exterior camera S5 is provided to monitor the situation outside of the vehicle (e.g., the situation in front of his or her own vehicle, in particular). A radar S6 is provided to measure the distance to an obstacle in front of the vehicle, for example. A navigation system S7 is provided to get map information and information about the vehicle's current location. A microphone S8 is provided to detect the speech uttered by an occupant (e.g., person(s) on the assistant's seat or the rear seat).

The controller U controls the various devices S11-S15 for the purpose of providing driving assistance to be described later. Specifically, a head-up display S11 is provided in front of the driver's seat. A loudspeaker S12 is provided to emit sound inside the vehicle cabin. An adaptive auto-cruise device S13 is provided to be operable in the entire vehicle speed range (i.e., from a very low speed of slightly more than 0 km/h to the maximum speed) according to an embodiment. A power steering device S14 is provided to perform automatic steering, in particular. A throttle actuator S15 is provided to allow the driver to control the throttle characteristic (specifically, control the throttle opening with respect to the accelerator position). Note that some of these sensors S1-S8 and devices S11-S15 may be unused according to the present invention (but are shown on the drawings as sensors and devices for use in a different type of control from that of the present invention).

To provide various types of driving assistance to be described later, the controller U includes a database D2. The database D2 stores information about the features of a road that entertained the driver. The database D2 is actually implemented as an externally connected storage device with a large storage capacity.

Next, it will be described how to classify the driver's condition as any of four types. First of all, the driver's degrees of focus on driving and his or her degree of leeway in driving will be described as a premise of this type classification.

The focus on driving may be represented, depending on the driver's behavioral pattern, by any of the four different degrees, which will be hereinafter referred to as first, second, third, and fourth degrees, respectively, for convenience sake. Specifically, the first degree represents an external (passive) focus on driving, i.e., a situation where the driver is forced to perform driving operations against his or her will, and is less motivated to drive, due to some external factors. The second degree represents an internal (active) focus on driving, i.e., an ideal situation where the driver is driving his or her vehicle at his or her own will and is highly motivated to drive. The third degree represents the driver's distraction from driving (such as operating the touchscreen of the navigation system or talking over his or her cellphone). The fourth degree represents the driver's loss of focus (which is defined to be a redundancy that is an unused, reserved portion of his or her maximum focusing ability and will be hereinafter referred to as a "spare capacity" in the following description and drawings).

Supposing the sum of these four degrees of focus is 100%, the degree of focus on driving is the percentage accounted for by the sum of the external and internal foci, and the driver's degree of leeway in driving is the percentage accounted for by the sum of the internal focus and the spare capacity.

Figure 2:
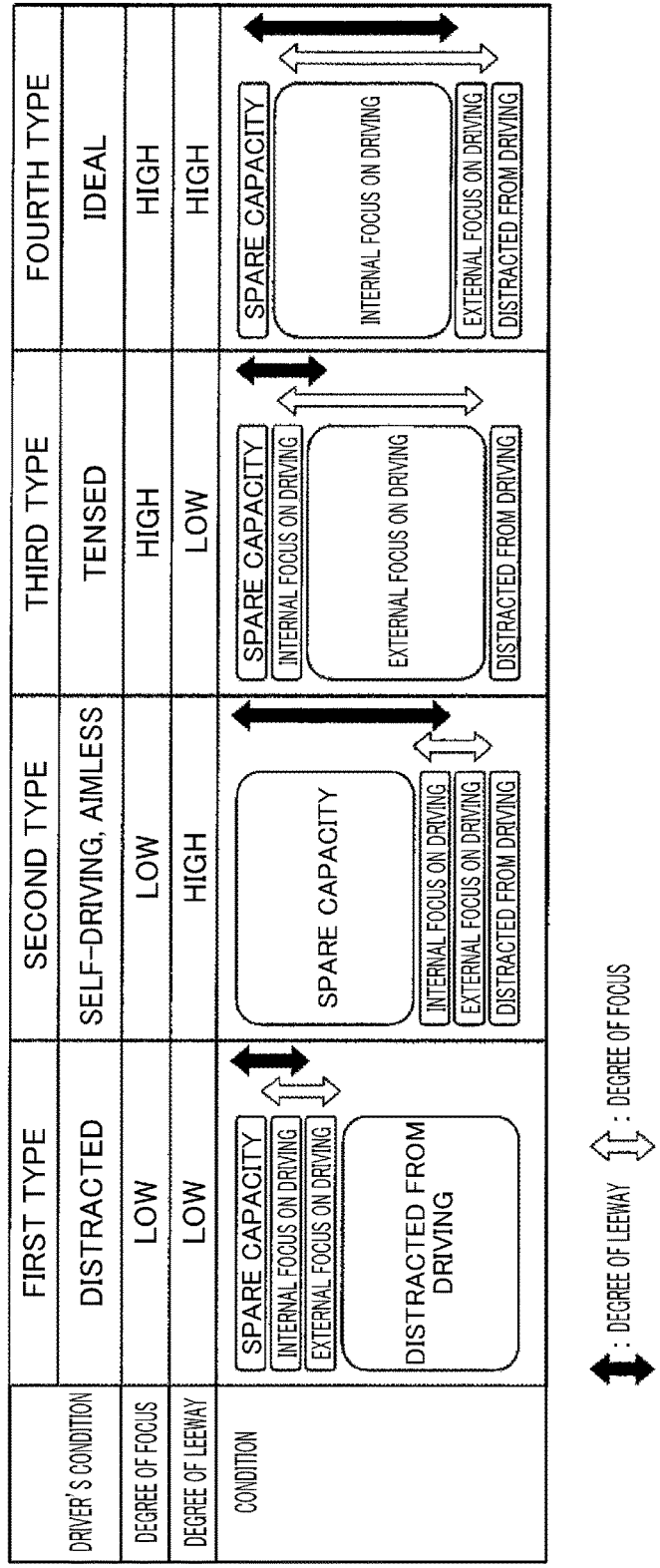
FIG. 2 A table summarizing the details of four different types of driver's condition.

The following first, second, third, and fourth types are defined as the four types as shown in FIG. 2. Specifically, the driver's condition is classified as the first type if his or her degree of focus on driving is low and his or her degree of leeway in driving is low (particularly when the driver is doing distracted driving (e.g., looking aside while driving his or her vehicle)). The driver's condition is classified as the second type if his or her degree of focus on driving is low and his or her degree of leeway in driving is high (e.g., when his or her vehicle is autonomous driving or when he or she is doing aimless driving). The driver's condition is classified as the third type if his or her degree of focus on driving is high and his or her degree of leeway in driving is low. The driver in this third type of condition is found tensed, for example, when the following vehicle is running close behind his or her vehicle. The driver's condition is classified as the fourth type if his or her degree of focus on driving is high and his or her degree of leeway in driving is high. This is an ideal driving condition.

FIG. 3 is a table summarizing how the driver's condition, including the degrees of external and internal foci, the degree of distraction from driving, and the degree of spare capacity, is determined based on various parameters. Examples of such parameters include the driver's physical features extracted from the image captured by the interior camera S4 such as his or her facial expressions, eye direction, and pupil state and how the accelerator pedal (A pedal) and brake pedal (B pedal) are operated. The driver's current condition is determined to be any of the four types based on these results of detection integrated together.

A vehicle according to the present invention is designed to be subjected to autonomous driving control (e.g., fully autonomous driving according to an embodiment). Thus, various kinds of control, including not only selection of a route to the destination but also control of the vehicle's position on the road that the vehicle is currently running on, and its stop, start, acceleration, deceleration, vehicle speed, passing and other vehicle behaviors (via automatic control of e.g., steering, braking and throttle), are carried out automatically. As for how to carry out autonomous driving, various methods have been proposed so far, and detailed description thereof will be omitted herein.

The controller U is designed to provide, in advance (i.e., before the autonomic driving is deactivated), driving assistance for the driver in such a way as to increase the driver's degree of internal focus on driving if the driver's degree of internal focus on driving is low when the deactivation of the autonomous driving is predicted. An exemplary procedure of control to be performed by the controller U will be described with reference to the flowcharts of FIGS. 4-7. In the following description, the reference sign Q denotes a processing step.

First of all, in Q1 shown in FIG. 4, the driver's condition is determined as will be described later. Next, in Q2, a determination is made whether or not the vehicle is autonomous driving now. If the answer to the question of Q2 is NO, then the process goes back to Q1.

On the other hand, if the answer to the question of Q2 is YES, then a determination is made whether or not the predicted accuracy value of a sensor essential for autonomous driving is equal to or less than a predetermined threshold value. In this processing step Q3, specifically, the determination is made based on a decline in the detection accuracy of a camera for use in autonomous driving to capture an image in front of the driver's own vehicle (e.g., a decline in detection accuracy due to the weather or a decline in the accuracy of detecting a traveling lane due to a dirty white line on the road) or on a decline in the detection accuracy of a GPS sensor for detecting the current location of the driver's own vehicle.

If the answer to the question of Q3 is NO, then the process goes back to Q1 (i.e., autonomous driving is continued). The answer to the question of Q3 becomes YES in a situation where it is not beneficial to continue autonomous driving as it is. In that case, in Q4, a determination is made whether or not the driver's degree (or level) of internal focus on driving is equal to or less than a predetermined threshold value (i.e., a determination is made whether or not there is a decline in the degree of internal focus). If the answer to the question of Q4 is NO (i.e., if the driver has a high degree of internal focus), then the driver is notified (e.g., with an audio alarm or alert message output from the loudspeaker S12), in Q5, that the autonomous driving will be deactivated soon, and then the autonomous driving is deactivated in Q6. If the process proceeds from Q4 to Q6 via Q5, then the driver has so high a degree of internal focus that he or she is ready to start driving operations as soon as the autonomous driving is deactivated.

On the other hand, if the answer to the question of Q4 is YES, performing the processing steps Q5 and Q6 would impose excessively heavy driving load on the driver immediately after the autonomous driving is deactivated, thus increasing the chances of causing some problems such as a delay in response in proper driving operations to take. In that case, control of increasing the driver's internal focus on driving is carried out in Q7 as will be described later. When this processing step Q7 is finished, the process will go back to Q1. Providing such driving assistance as to increase the internal focus in Q7 enhances the driver's internal focus. After that, the answer to the question of Q4 will become NO, and the process will proceed in the order of Q5 and Q6.

Alternatively, after the processing step Q7 is performed for a predetermined amount of time, the process may proceed to Q5 without going back to Q1. Still alternatively, after the processing step Q7 is done, the processing of detecting (or estimating) the driver's degree of internal focus may be performed as in Q1, and then the process may go back to Q4. Even in that case, the process may also proceed to Q5 after the processing step Q7 is performed for a predetermined amount of time.

Figure 4:
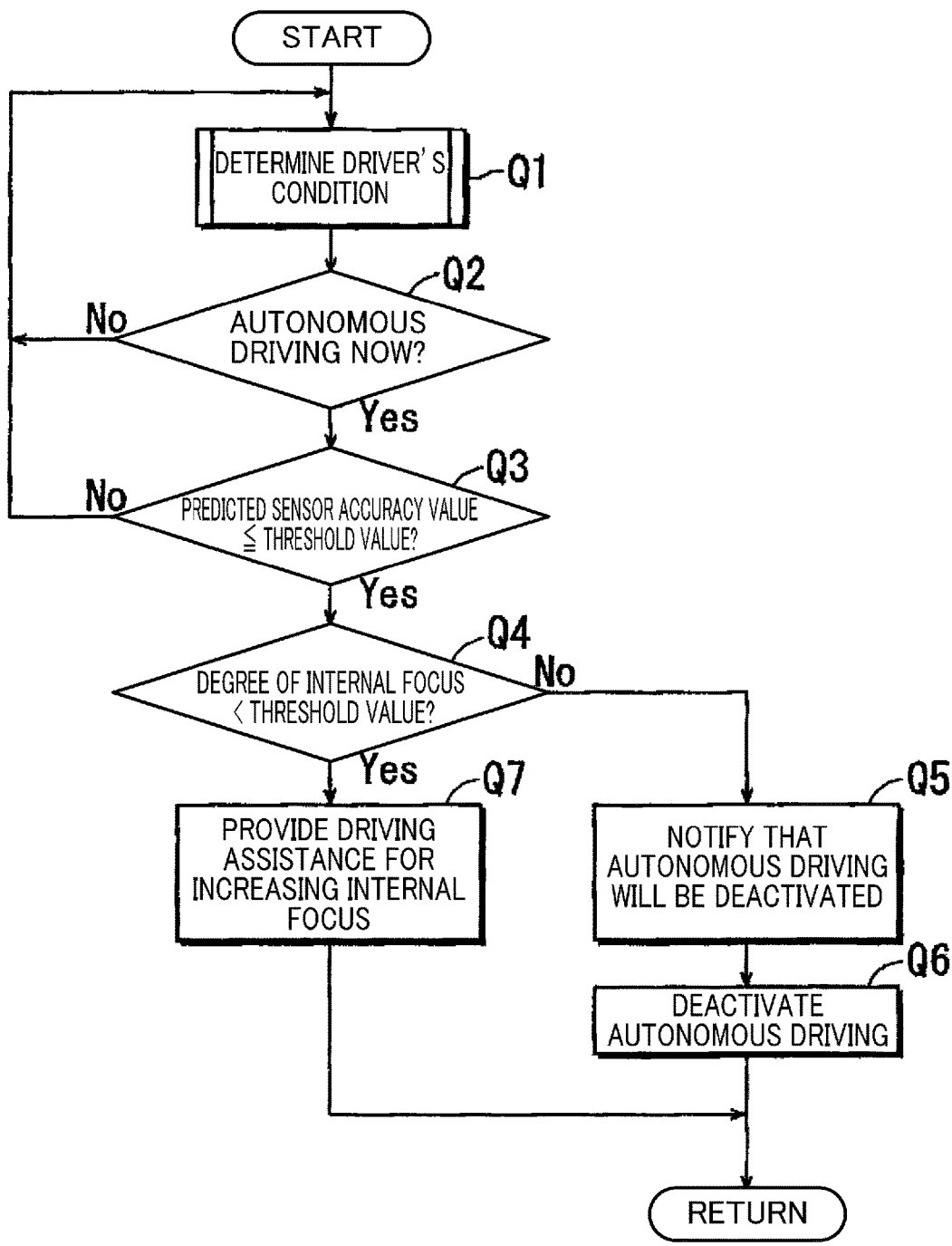
FIG. 4 A flow chart illustrating an exemplary control procedure according to the present invention.
Figure 5:
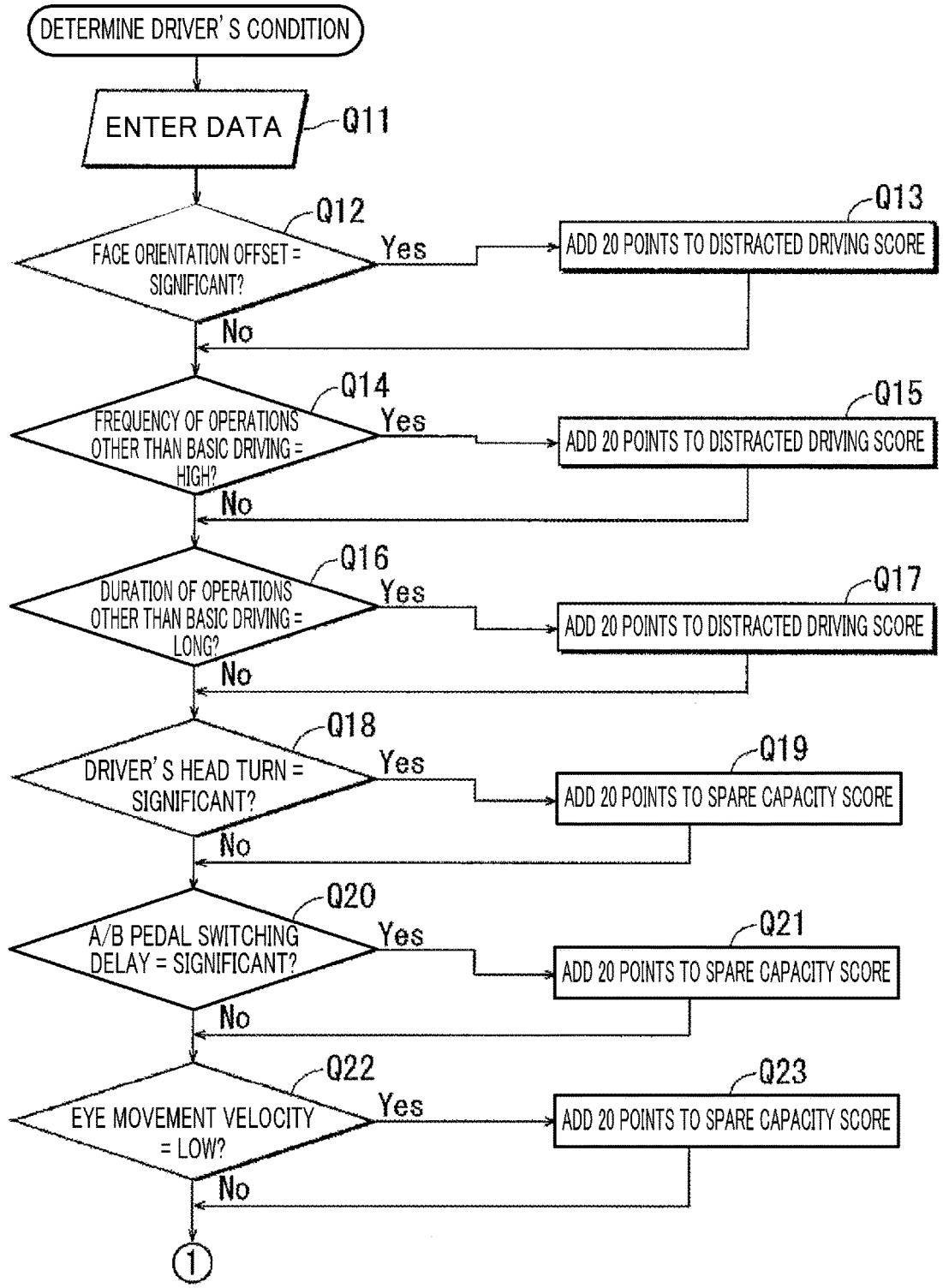
FIG. 5 A flowchart illustrating a detailed procedure of the driver's condition determination step shown in FIG. 4
Figure 6:
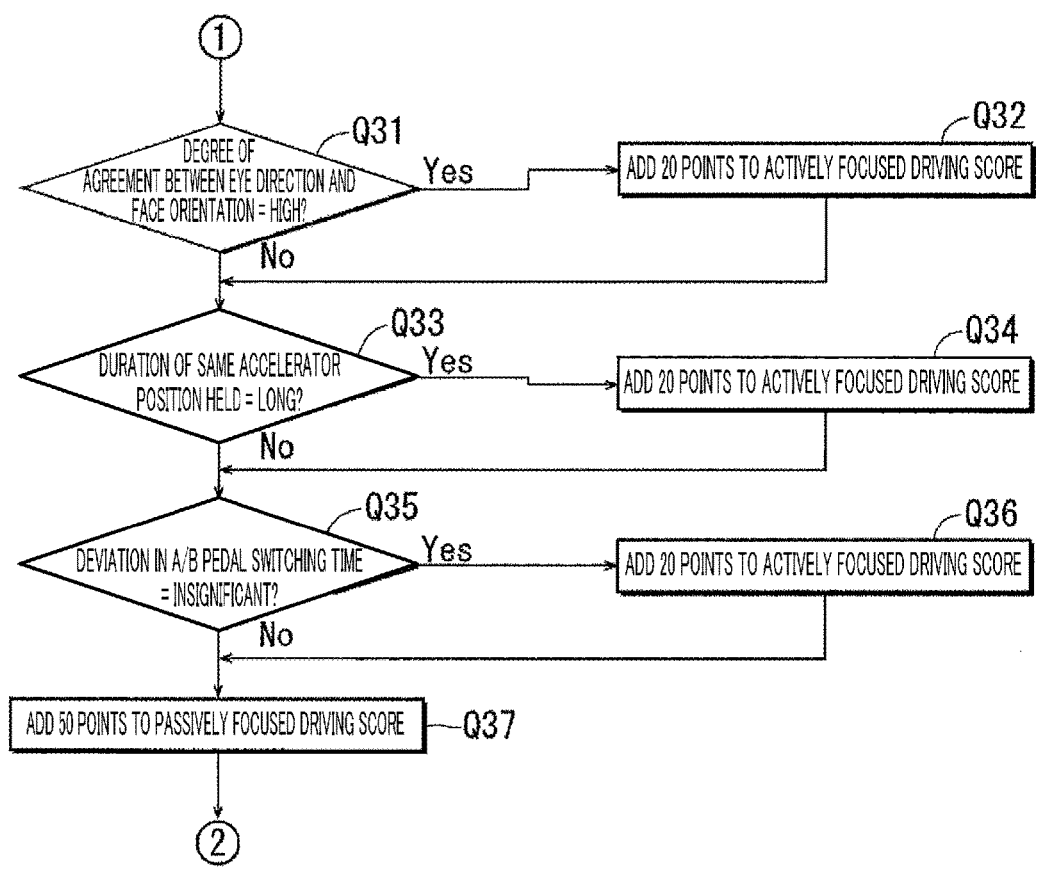
FIG. 6 A flow chart illustrating a set of processing steps that follow the ones shown in FIG. 5.
Figure 7:
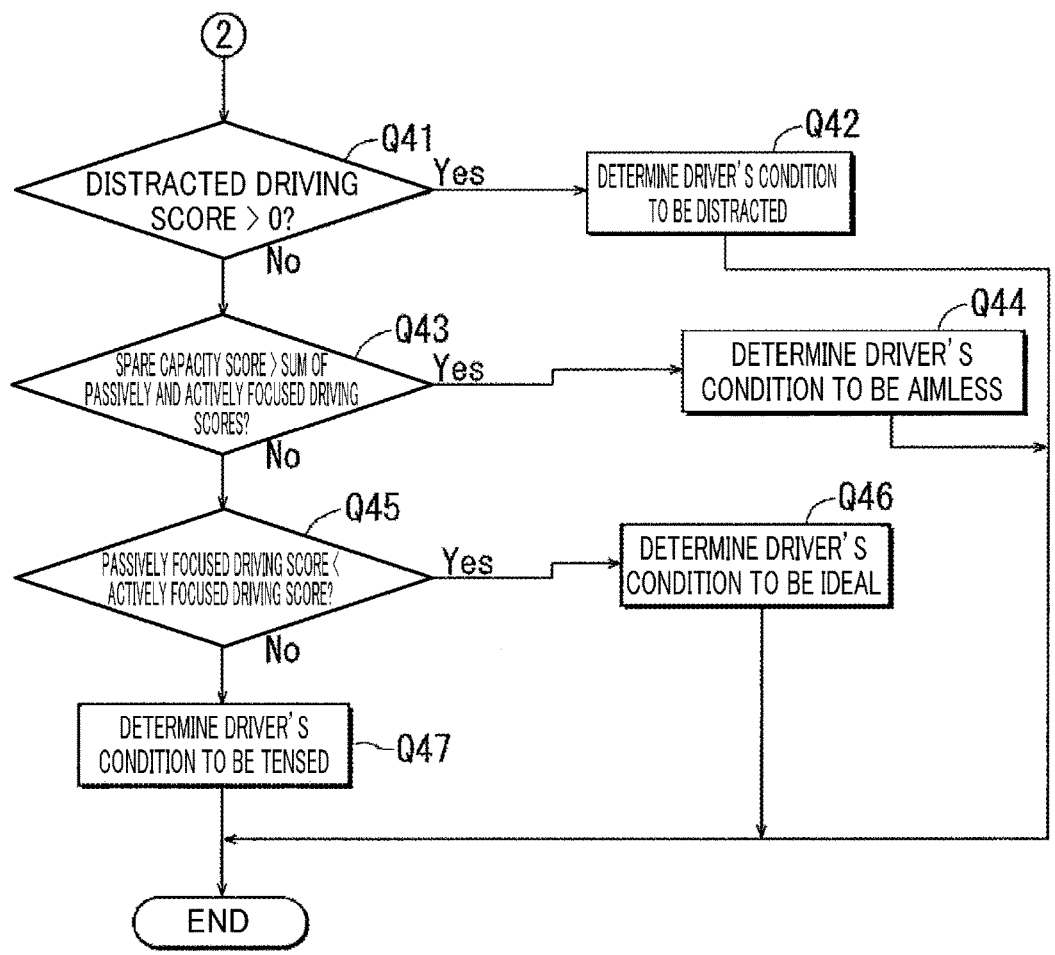
FIG. 7 A flow chart illustrating a set of processing steps that follow the ones shown in FIG. 6.

FIGS. 5-7 show the details of Q1 shown in FIG. 4. Specifically, after data has been entered in Q11 shown in FIG. 5, the controller U determines in Q12 whether or not the driver's face orientation has a significant offset (i.e., whether or not he or she is looking aside while driving). If the answer to the question of Q12 is YES, then a predetermined number of points (e.g., 20 points) are added to a distracted driving score in Q13.

After Q13 or if the answer to the question of Q12 is NO, a determination is made in Q14 whether or not the driver is frequently performing operations other than basic driving operations (i.e., pumping the accelerator and brake pedals, turning the steering wheel, and other driving operations to change the vehicle's behavior). More specifically, a determination is made whether or not the frequency of occurrence of such non-basic operations is equal to or greater than a predetermined threshold value. If the answer to the question of Q14 is YES, then a predetermined number of points (e.g., 20 points) are added to the distracted driving score in Q15.

After Q15 or if the answer to the question of Q14 is NO, a determination is made in Q16 whether or not the duration of those other operations is significantly long compared to that of the basic driving operations. More specifically, a determination is made whether or not the duration is equal to or greater than a predetermined threshold value. If the answer to the question of Q16 is YES, then a predetermined number of points (e.g., 20 points) are added to the distracted driving score in Q17.

After Q17 or if the answer to the question of Q16 is NO, a determination is made in Q18 whether or not the driver's head turn is significant. More specifically, a determination is made whether or not his or her head turn is equal to or greater than a predetermined threshold value. If the answer to the question of Q18 is YES, then a predetermined number of points (e.g., 20 points) are added to a spare capacity score in Q19.

After Q19 or if the answer to the question of Q18 is NO, a determination is made in Q20 whether or not a significant delay has been caused in changing the pedals to pump from the accelerator pedal to the brake pedal, and vice versa. More specifically, a determination is made whether or not the delay is equal to or greater than a predetermined threshold value. If the answer to the question of Q20 is YES, then a predetermined number of points (e.g., 20 points) are added to a spare capacity score in Q21.

After Q21 or if the answer to the question of Q20 is NO, a determination is made in Q22 whether or not the driver's eye movement velocity is low. More specifically, a determination is made whether or not the eye movement velocity is equal to or smaller than a predetermined threshold value. If the answer to the question of Q22 is YES, then a predetermined number of points (e.g., 20 points) are added to a spare capacity score in Q23.

After Q23 or if the answer to the question of Q22 is NO, a determination is made in Q31 shown in FIG. 6 whether or not the degree of agreement between the driver's face orientation and his or her eye direction is high. More specifically, a determination is made whether or not the degree of agreement falls within a predetermined threshold range. If the answer to the question of Q31 is YES, then a predetermined number of points (e.g., 20 points) are added to an actively (internally) focused driving score in Q32.

After Q32 or if the answer to the question of Q31 is NO, a determination is made in Q33 whether or not the same accelerator position has been held for a significant amount of time. More specifically, a determination is made whether or not the amount of time is equal to or greater than a predetermined threshold value. If the answer to the question of Q33 is YES, then a predetermined number of points (e.g., 20 points) are added to an actively (internally) focused driving score in Q34.

After Q34 or if the answer to the question of Q33 is NO, a determination is made in Q35 whether or not the deviation (i.e., the standard deviation) in the amount of time it takes for the driver to change pedals to pump from the accelerator pedal to the brake pedal, and vice versa, is insignificant. More specifically, a determination is made whether or not the standard deviation is equal to or smaller than a predetermined threshold value. If the answer to the question of Q35 is YES, then a predetermined number of points (e.g., 20 points) are added to an actively (internally) focused driving score in Q36. If the total number of points added in the processing steps Q32, Q34, and Q36 is equal to or less than a predetermined threshold value, then the answer to the question in Q4 shown in FIG. 4 becomes YES.

If the answer to the question of Q35 is NO, then a predetermined number of points (e.g., 50 points) are added to a passively (externally) focused driving score in Q37.

After having performed the processing step Q37, a determination is made in Q41 shown in FIG. 7 whether or not the (total) distracted driving score is greater than 0 points. If the answer to the question of Q41 is YES, then a decision is made in Q42 that the driver is doing distracted driving (e.g., looking aside while driving), i.e., the driver's current condition falls under the first type.

On the other hand, if the answer to the question of Q41 is NO, then a determination is made in Q43 whether or not the (total) spare capacity score is greater than the sum of the (total) passively focused driving score and the (total) actively focused driving score. If the answer to the question of Q43 is YES, then a decision is made in Q44 that the driver is doing aimless driving, i.e., the driver's current condition falls under the second type.

On the other hand, if the answer to the question of Q43 is NO, then a determination is made in Q45 whether or not the (total) actively focused driving score is greater than the (total) passively focused driving score. If the answer to the question of Q45 is YES, then a decision is made in Q46 that the driver is in an ideal condition, i.e., the driver's current condition falls under the fourth type. On the other hand, if the answer to the question of Q45 is NO, then a decision is made in Q47 that the driver is in a tense condition, i.e., the driver's current condition falls under the third type.

Figure 8:
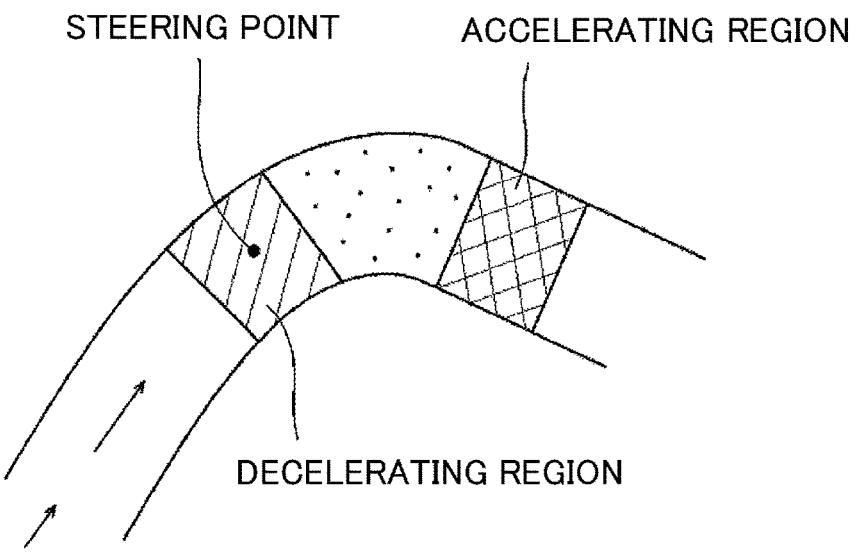
FIG. 8 Diagrammatically illustrates exemplary control for enhancing the driver's motivation to drive.

Next, an exemplary driving assistance technique for increasing the driver's internal focus on driving in Q7 shown in FIG. 4 will be described with reference to FIGS. 8-10. Specifically, FIG. 8 illustrates an embodiment in which exemplary driving instructions are displayed on the screen to the driver. Such driving instructions may be displayed on the screen of the navigation system S7 or on the head-up display S11. For example, while the driver is making cornering, not only an accelerating region and a decelerating region (in two different colors, for example) but also a steering point indicating a steering start timing (in a flickering state, for example) may be highlighted on the road image displayed. This enhances the driver's motivation to drive and improves his or her driving skills as well. Although an exemplary cornering technique is illustrated in FIG. 8, any other appropriate set of exemplary driving instructions may also be displayed as an ideal example to follow, which may be a set of exemplary driving operations to perform on a highway or a set of exemplary parking operations, depending on the real-time situation on the road. Among other things, it is particularly beneficial to display a steering timing and timings to depress the accelerator and brake pedals as examples to follow. Optionally, the driver may be notified of these timings through audio guidance.

Figure 9:
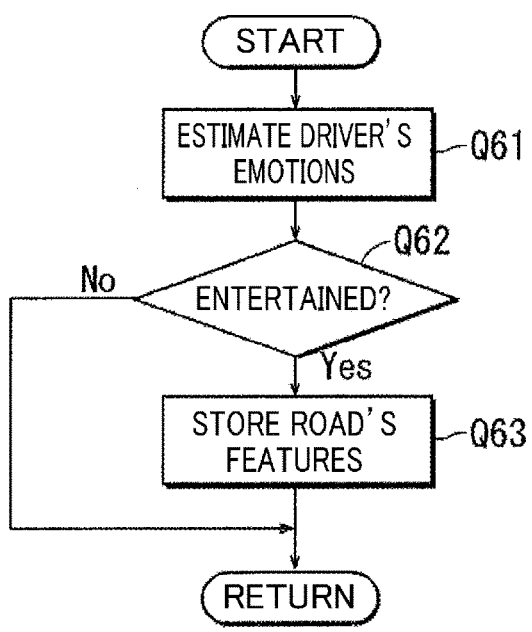
FIG. 9 A flowchart illustrating an exemplary procedure of control for storing the features of a road that entertained the driver.

FIG. 9 shows, as an example of driving assistance for increasing the internal focus, an exemplary procedure of control to be performed to provide navigation to a road with features that would entertain the driver. Specifically, in Q61, the driver's emotions are estimated based on his or her facial expressions captured by the interior camera S4, for example. Next, in Q62, a determination is made, based on the results of estimation obtained in Q61, whether or not the driver is enjoying driving, i.e., entertained or amused by the features of the road. If the answer to the question of Q62 is YES, the features of the road entertaining him or her are stored in the database D2. On the other hand, if the answer to the question of Q62 is NO, then the process returns with the processing step Q63 skipped. Then, in Q4 shown in FIG. 4, the controller U selects, from among a plurality of roads running in almost the same direction as the road currently taken, a road having the features stored in the database D2, and provides navigation to this selected road (e.g., by providing guidance on the navigation screen).

Figure 10:
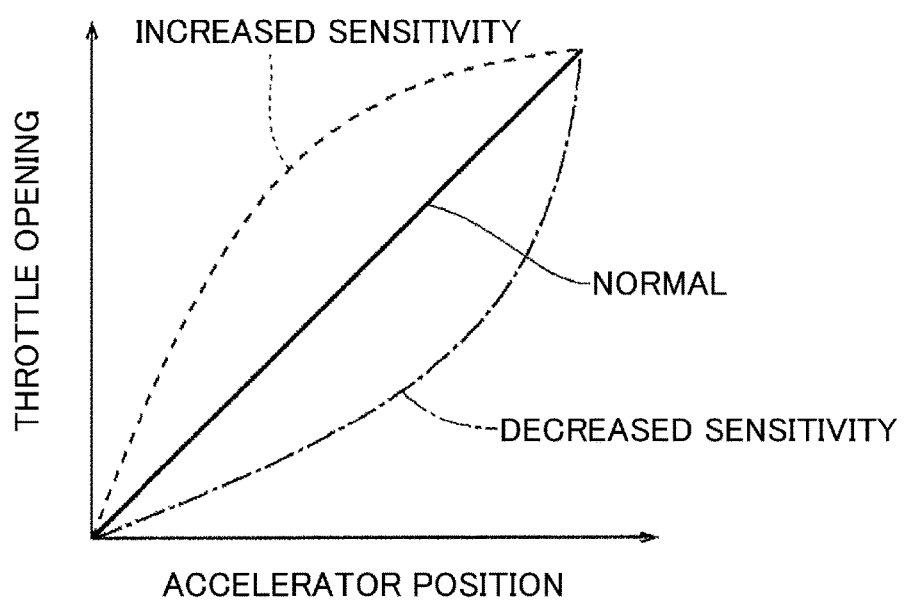
FIG. 10 Diagrammatically illustrates how the throttle characteristics may be changed.

FIG. 10 illustrates, as another example of driving assistance for increasing the internal focus, an exemplary technique for enhancing the driver's motivation to drive by increasing the sensitivity of an engine output to accelerating operations. In FIG. 10, the solid line represents a normal (ordinary) throttle characteristic. The broken curve represents a throttle characteristic with increased sensitivity (i.e., a characteristic that the throttle opening increases more significantly with respect to the same accelerator position than in the normal throttle characteristic). The one-dot-chain curve represents a throttle characteristic with decreased sensitivity (i.e., a characteristic that the throttle opening decreases more significantly with respect to the same accelerator position than in the normal throttle characteristic). In Q4 shown in FIG. 4, the throttle characteristic with the increased sensitivity as indicated by the broken curve in FIG. 10 is selected, and the throttle actuator S15 is controlled in accordance with this selected throttle characteristic. Optionally, any two or all three of the control procedures shown in FIGS. 8-10 may be performed.

Naturally, the driving assistance for increasing the driver's internal focus on driving does not have to be as described above, but may also be any other appropriate one. First, the steering characteristic may be changed. Specifically, the steering characteristic may be changed such that the actual steering angle of the steering wheel increases if the rudder angle remains the same. Optionally, the sensitivity may also be increased by reducing the operation reaction force of the accelerator pedal or the steering wheel.

Alternatively, to increase the internal focus, at least one of engine sound, wind noise or road noise (i.e., a shriek of tires) may be output at an amplified volume from the loudspeaker S12 into the vehicle cabin. Such a sound or noise output from the loudspeaker S12 may be either an actual sound or noise detected by a microphone and then amplified or a fake sound at an amplified volume. These various types of control for increasing the internal focus may be performed in any arbitrary combination. Alternatively, any appropriate technique other than these may also be adopted.

Although some embodiments of the present invention have been described, the present invention is in no way limited to those exemplary embodiments but may be changed, replaced or modified appropriately without departing from the true spirit and scope of the present invention as defined only by the appended claims. The parameters used to classify the driver's condition as any of the four types shown in FIG. 2 may be only some of the ones shown in FIG. 3 or may further include any other appropriate parameter such as a one indicating a steering operation state. The driving assistance is suitably ended gradually. For example, if the driving assistance is provided as an amplified moving vehicle noise, then the degree of the amplification is suitably gradually decreased. Furthermore, each of the processing steps or each series of processing steps shown in the flowcharts represents any of the functions of the controller U. Thus, any of these functions may also be embodied as a hardware component that forms part of the controller U if the step or the series of steps is implemented as a means or section for performing its/their intended function. Naturally, objects of the present invention include not only the explicitly specified ones but also others that are implicitly suggested herein as advantages or benefits of the present disclosure.

INDUSTRIAL APPLICABILITY

The present invention is useful for safe deactivation of autonomous driving.

DESCRIPTION OF REFERENCE CHARACTERS

U: Controller
D2: Database
S1: Acceleration Sensor
S2: Brake Sensor
S3: Steering Angle Sensor
S4: Interior Camera (for detecting degree of focus on driving and emotion such as pleasure)
S5: Exterior Camera (for detecting surrounding situations)
S6: Radar
S7: Navigation system
S8: Microphone
S11: Head-up display
S12: Loudspeaker
S13: Auto-Cruise Device
S14: Power-Steering device
S15: Throttle Actuator

The invention claimed is:

1. A driving assistance device for use in a vehicle with autonomous driving capabilities, the device comprising:
a degree of internal focus estimating unit configured to estimate a driver's degree of internal focus on driving;
a deactivation predicting unit configured to predict deactivation of autonomous driving; and
a driving assistance unit configured to provide driving assistance for the driver in such a way as to increase the driver's degree of internal focus on driving if the degree of internal focus on driving is estimated to be low by the degree of internal focus estimating unit when the deactivation of the autonomous driving is predicted by the deactivation predicting unit, wherein
the driving assistance unit performs a control of increasing sensitivity to a change in the vehicle's state in response to driving operations.

2. The driving assistance device of claim 1, wherein the driving assistance unit provides navigation to a road with features that would entertain the driver through driving.

3. The driving assistance device of claim 1, wherein the driving assistance unit gives guidance in exemplary driving operations.

4. The driving assistance device of claim 1, wherein the driving assistance unit performs control of boosting moving vehicle noise inside the vehicle's cabin.

5. The driving assistance device of claim 1, wherein if the degree of internal focus on driving is estimated to be high by the degree of internal focus estimating unit when the deactivation of the autonomous driving is predicted by the deactivation predicting unit, then the driver is just notified that the autonomous driving will be deactivated without being provided with any driving assistance by the driving assistance unit, and then the autonomous driving is deactivated.

6. The driving assistance device of claim 1, wherein the deactivation predicting unit predicts the deactivation of the autonomous driving according to a degree of accuracy of information available and necessary for the autonomous driving.

7. The driving assistance device of claim 1, wherein the driving assistance unit performs a control of increasing sensitivity to a change in the vehicle's state in response to accelerating operations and/or steering operations.

8. The driving assistance device of claim 1, wherein the driving assistance unit increases the sensitivity of an engine output to accelerating operations.

9. The driving assistance device of claim 1, wherein the driving assistance unit changes the steering characteristic such that the actual steering angle of the steering wheel increases.

10. The driving assistance device of claim 1, wherein the driving assistance unit increases the sensitivity of steering operations by reducing the operation reaction force of the accelerator pedal or the steering wheel.

* * * * *